United States Patent [19]

Takashima

[11] Patent Number: 5,791,901
[45] Date of Patent: Aug. 11, 1998

[54] ARTIFICIAL TOOTH AND MANUFACTURING METHOD OF AN ACRYLIC RESIN DENTURE

[76] Inventor: Masayuki Takashima, 32-5 Nakao Shitamachi, Arashiyama, Nishikyo-ku, Kyoto, Japan

[21] Appl. No.: 740,214

[22] Filed: Oct. 25, 1996

[30] Foreign Application Priority Data

Oct. 27, 1995 [JP] Japan .................. 7-303537

[51] Int. Cl.$^6$ ............................................ A61C 13/08
[52] U.S. Cl. ..................... 433/212.1; 433/213; 433/195
[58] Field of Search ............................. 433/191, 193, 433/195, 202.1, 212.1, 213, 201.1

[56] References Cited

U.S. PATENT DOCUMENTS

| | | | |
|---|---|---|---|
| 2,920,390 | 1/1960 | Saffir | 433/212.1 |
| 4,529,384 | 7/1985 | Severy | 433/213 |
| 4,689,013 | 8/1987 | Lustig | 433/213 |
| 5,007,836 | 4/1991 | Gayso | 433/213 |
| 5,320,533 | 6/1994 | Lee | 433/218 |
| 5,346,396 | 9/1994 | Hakamatsuka | 433/202.1 |
| 5,415,546 | 5/1995 | Cox, Sr. | 433/213 |

*Primary Examiner*—Nicholas D. Lucchesi
*Attorney, Agent, or Firm*—Thompson Hine & Flory LLP

[57] ABSTRACT

Disclosed is an artificial tooth that is structured such that the tooth is firmly held in its proper position in a core until a plate resin is fully polymerized and cured in succession to the manufacture of a wax denture. To this end, the artificial tooth has on its portion to be embedded into the core a projection for a temporary bond with the core. Also disclosed is a manufacturing method of an acrylic resin denture comprising the steps of forming a projection for a temporary bond with a core, on the portion of a finished artificial tooth to be -embedded into a core material before the finished artificial tooth is embedded into the core by applying a drop of resin that is of the same type as the material of the artificial tooth, and the step of removing the core along with the projection after a plate resin is polymerized. Instead of the application of a resin drop, a resin pellet can be glued on the portion of the finished artificial tooth to be embedded into a core material before the finished artificial tooth is embedded into the core.

8 Claims, 3 Drawing Sheets

ARTIFICIAL TOOTH AND MANUFACTURING METHOD OF AN ACRYLIC RESIN DENTURE

BACKGROUND OF THE INVENTION

1. Field of the invention

The present invention relates to the structure of an artificial tooth for use in an acrylic resin denture that is manufactured using a lost wax technique. Misalignment and dislocation of an artificial tooth from a core (mold) must be avoided in the process of wax removal step. In view of this, the present invention provides a new artificial tooth that has a structure allowing a temporary bond of the artificial tooth to its core. The present invention also relates to the method of manufacturing the acrylic resin denture.

2. Description of the Related Art

The manufacturing process of an acrylic resin denture using a lost wax technique comprises a plurality of steps: a step of manufacturing a wax denture, in which artificial teeth are arranged on a wax plate that is formed by making impressions of a tooth in the mouth of a patient using wax and then the occlusion of the artificial teeth are adjusted, a step of embedding wax denture into a core material such as plaster, a core manufacturing step in which wax is removed from the denture after the core material is cured, a step of filling plate resin in the core, and a step of removing the core after the plate resin is polymerized. A variety of methods from a diversity of viewpoints have been proposed in the steps of embedding the wax denture into the core material and filling and polymerization of the plate resin; for example, the materials of the acrylic resin denture and their curing and polymerization conditions are identified to improve dimensional accuracy of the acrylic resin denture, to enhance a fit of the acrylic resin denture in the mouth and to correct cure distortions of the core material and plate resin.

There has not been a concept that teeth aligned in the wax denture according to occlusal adjustment are positively bonded to the core. Specifically, in the above series of process steps, the artificial tooth is held in the core during wax removal, both appliances provide no affinity therebetween because of the difference in material. Both appliances are not chemically bonded. The surface contour of the artificial tooth does not help enhance physical bonding between both appliances. The core must be detached from the acrylic resin denture in the final process step. The weak bonding is advantageous in view of job efficiency. On the other hand, prior to the final process step, both appliances are subject to detachment under vibrations and shocks in the middle of process steps. This possibly leads to a more serious defect such as the misalignment or dislocation of the artificial tooth in the acrylic resin denture.

When a double embedding technique is used as an embedding procedure of the wax denture, the core after wax removal is split into two: a primary embedding side and a secondary embedding side. In this case, the counterdie of the core is observed. Thus, the misalignment or dislocation of the artificial tooth is detected. An extra step, thus extra time, is taken for re-fixing the dislocated artificial tooth to the core with an adhesive. If an adhesive is used, the artificial tooth is raised by the thickness of the adhesive used, the fit of the acrylic resin denture is degraded, and working efficiency in the core removal in the final step process is lowered. In another method of embedding procedure, a wax denture is embedded in a lump using injection molding. In this method, the counterdie of the core cannot be observed in the middle of the process. Even if the artificial tooth suffers misalignment or dislocation, it goes undetected, and then the plate resin undergoes filling and polymerization. As a result, defective dentures are unnecessarily produced with a poor production yield.

SUMMARY OF THE INVENTION

It is an object of the present invention to provide an artificial tooth that is structured such that the tooth is firmly held in its proper position in a core until a plate resin is fully polymerized and cured in succession to the manufacture of an wax denture.

It is an object of the present invention to provide a manufacturing method of an acrylic resin denture which, as necessary, imparts to the acrylic resin denture the structure that helps hold temporarily the artificial tooth in the core and easily removes the structure from the acrylic resin denture.

To achieve the above objects, according to the present invention, an artificial tooth has a projection for temporary bond with the core that is formed by curing the core material. Specifically, the projection is formed by applying a drop of resin on an existing artificial tooth, wherein the drop of resin is of the same material as the existing artificial tooth. Alternatively, the projection is formed by gluing a resin pellet onto an artificial tooth. By "a projection for temporary bond with the core" is meant that the projection serves as a clasp to hold the artificial tooth in the core until the plate resin is fully polymerized in the course of the manufacture of the acrylic resin denture and that the projection is removed from the artificial tooth when the core is removed in the final stage of the manufacture of the denture. The number and size of the projections in use are preferably small on condition that the projections have a bonding strength with the core to the extent that the artificial tooth remains attached against vibrations and shocks applied in the course of the manufacture of the denture.

In the method of manufacturing an acrylic resin denture, before an artificial tooth is embedded into a core material, a drop of resin of the same material is applied to part of the artificial tooth to be embedded into the core to form a projection for temporal engagement with the core, and the projection is removed along with the core after the plate resin is removed. Alternatively, the projection is formed by gluing a resin pellet onto an artificial tooth.

DETAILED DESCRIPTION OF THE PREFERRED EMBODIMENTS

Figure 1:
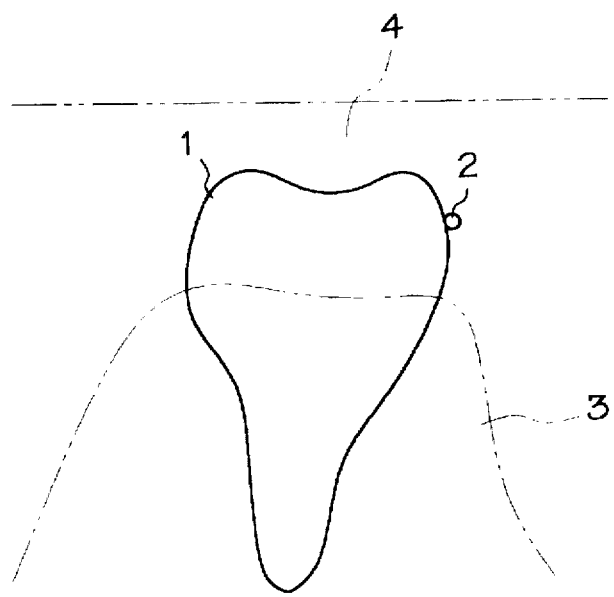
FIG. 1 is a front view showing generally an artificial tooth in one embodiment of the present invention.

Referring to the drawings, the preferred embodiments of the present invention are now discussed. The embodiments of an artificial tooth are discussed first. FIG. 1 generally shows the artificial tooth of this embodiment of the present invention. In its basic structure, a normal form artificial tooth 1 that is selected to match a tooth is provided with a projection 2 as shown in FIG. 1. Part of the artificial tooth 1 on which the Projection 2 is formed is a portion that can be exposed out of a wax plate 3 in the course of manufacturing a wax denture, namely, a portion that can be embedded into a core material, and thus in contact with a core 4. By forming the projection 2 in the embedded portion of the artificial tooth 1, the projection 2 is engaged with the core 4, and thus the artificial tooth 1 remains connected to the core 4. Namely, the projection 2 physically bonds the artificial tooth 1 with the core 4. The artificial tooth 1 is thus held in a proper position according to occlusal adjustment during the manufacture of the wax denture until the final process step in which the core 4 is removed.

The projection 2 may be formed at any position on the artificial tooth 1 as long as it is in contact with the core 4. The artificial tooth 1 is described herein in view of a try-in condition in wax denture stage and a correction of the artificial tooth 1 in the occlusal adjustment. To achieve a satisfactory try-in condition, the projection 2 is preferably formed on the front face of the artificial tooth 1 facing the lips if a disorder lies in the front tooth in order not to give the feeling of a foreign body to a patient. If a disorder lies in a molar, however, the position of the projection 2 in the molar is not so critical as in front teeth according to the experience of the inventor. This is because the tip of the tongue, which is the most sensitive portion, is less likely to touch the molar than the front teeth. Thus, even if the projection 2 is attached on the inner side of the artificial tooth 1 facing the tongue, the feeling of a foreign object is weak. When occlusal adjustment is performed, the artificial tooth 1 is corrected possibly by partly cutting, and thus the position of the projection 2 should avoid the correction portion of the artificial tooth 1. Specifically, if a front tooth suffers a disorder, the projection 2 is preferably formed near one of the side faces of the artificial tooth 1. In case of a molar tooth, the projection 2 is preferably formed near the center of the front face of the artificial tooth 1 facing the lips. This is because such locations are less likely to be corrected than the rest of the artificial tooth. Furthermore, in case of a diseased front tooth, two projections may be formed one near the left side face and the other near the right side face of the artificial tooth.

Figure 2A:
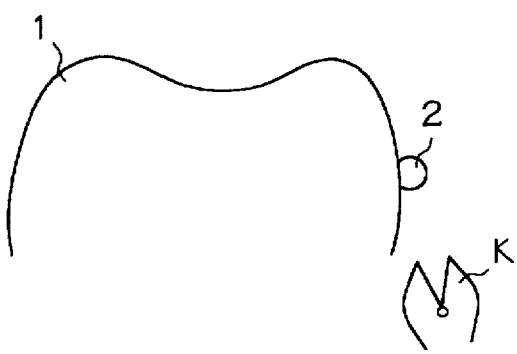
FIGS. 2A and 2B are front views showing specific configurations of the projections.
Figure 2B:
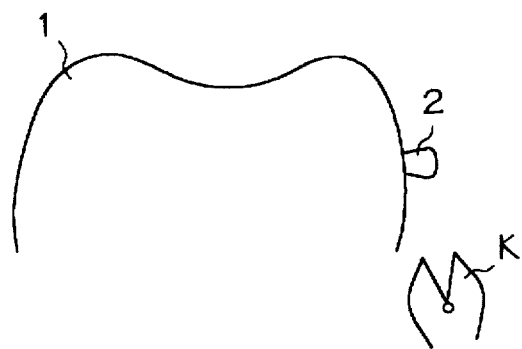

The shape of the projection 2 is now discussed. As shown in FIG. 2, the projection 2 may be a waterdrop shape (FIG. 2A) or dove-tail shape (FIG. 2B). These shapes of the projection increase a bonding strength between the artificial tooth 1 and the core 4.

In the final process step in succession to polymerization of the plate resin in the manufacture of the denture, the core 4 is removed, and the acrylic resin denture is finished by polishing step. At the same time, the projection 2 along with the core 4 is removed. The projection 2 is intended to provide temporary bond between artificial tooth 1 and the core 4 in the manufacture of the denture from the step of embedding the artificial tooth 1 in the core material to the step of polymerization of the plate resin. As shown in FIGS. 2A and 2B, the projection 2 has a smaller joint portion in cross section to the artificial tooth 1, and is thus easily removed, for example by cutting at the joint portion using forceps K.

The projection 2 may be integrally attached to the artificial tooth 1 during the formation of the artificial tooth 1, or may be attached to a finished artificial tooth in the course of manufacturing an acrylic resin denture. The object of the invention is equally achieved in both procedures. The latter procedure is discussed below.

The manufacturing method of the acrylic resin denture of the present invention is now discussed. Most of the procedure of the production of the acrylic resin denture of the present invention follows a typical manufacturing method. Namely, the present invention follows the prior art procedure from the step of making impressions of a tooth in the mouth of a patient using wax to the step of removing the core, except that the projection is attached to the artificial tooth that is contact with the core, to temporarily engage the artificial tooth with the core during the manufacture of the denture. In the discussion that follows, the projection is attached to the finished artificial tooth before the wax denture is embedded in the core material.

Figure 3:
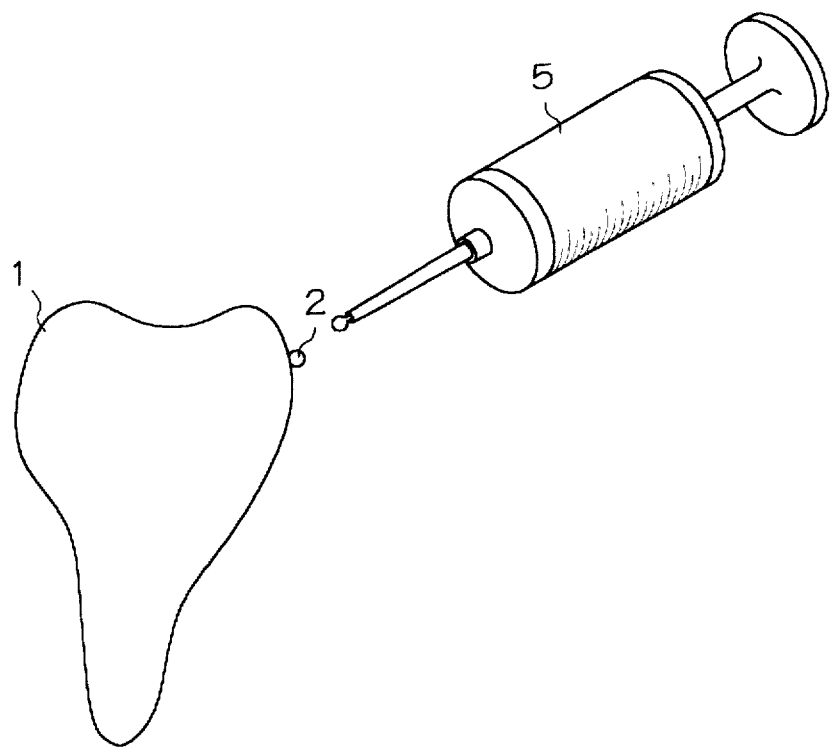
FIG. 3 is a front view showing the manufacturing method of an acrylic resin denture according to a first embodiment of the present invention.

FIG. 3 shows the first embodiment of the manufacturing method of the acrylic resin denture. To form a projection, a drop of resin is applied to a point on the portion of the artificial tooth 1 covered by the core material, using an injector 5. In this method, a waterdrop-shaped projection 2 shown in FIG. 2A is formed on the artificial tooth 1. The material of resin is not limited to any particular resin, because the artificial tooth 1 is physically connected to the core 4. To increase a bonding strength of the projection 2 to the artificial tooth 1, both are preferably of the same type of resin. To shorten the manufacture of the denture, a quick-drying resin is preferred.

Figure 4:
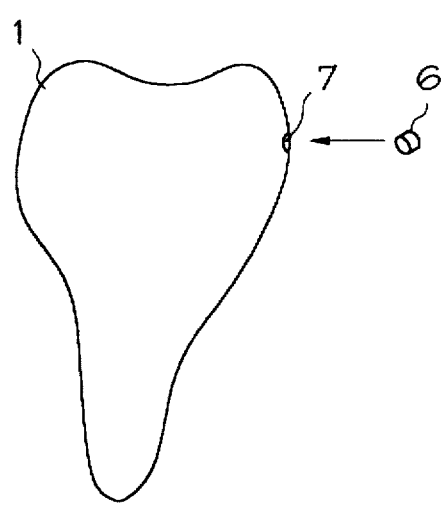
FIG. 4 is a front view showing the manufacturing method of the acrylic resin denture according to a second embodiment of the present invention.
Figure 5:
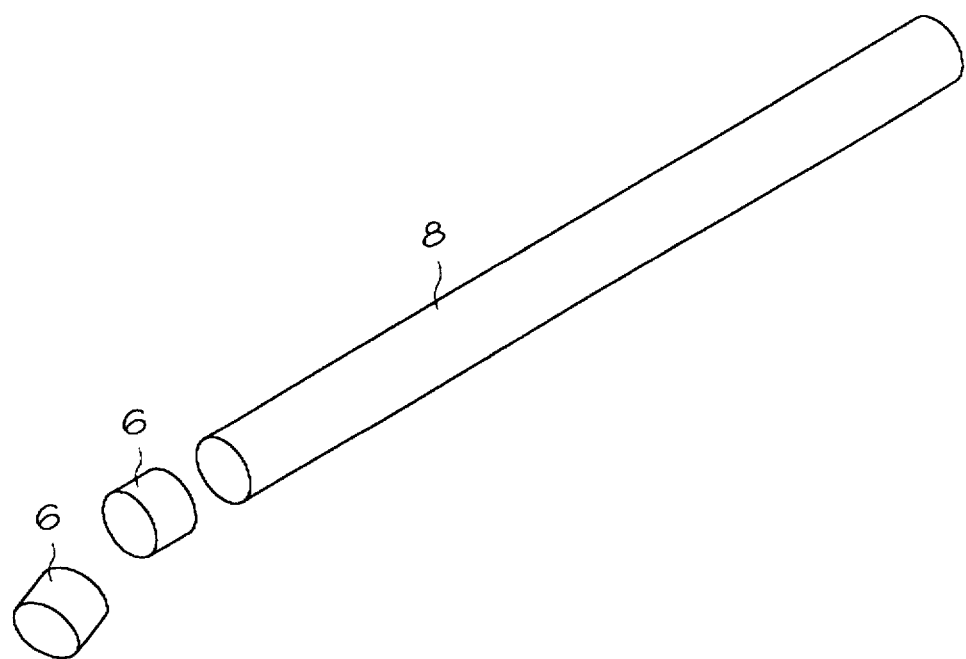
FIG. 5 is a perspective view showing the manufacturing step of the pellet.

In the second embodiment in FIG. 4, the projection 2 is formed by gluing a resin pellet 6 to the artificial tooth 1 with an adhesive 7. The pellet 6 is formed by cutting a resin bar 8 into pellets 6 of an appropriate size as shown in FIG. 5. The pellets 6 are preferably as small as possible but still sufficiently large enough to provide engagement between the artificial tooth 1 and the core. The smaller the pellet 6, the narrower the application area of the adhesive 7, and the easier the removal operation of the pellet 6 from the artificial tooth 1. In this method, the projection 2 is glued onto the artificial tooth 1 with the adhesive 7 only. The removal operation is easier, because the polishing operation in the final process step is polishing away the cured adhesive 7.

The projection 2 formed on the artificial tooth 1 finds another application. Dentists and dental laboratory technicians must use frequently a dental engine to cut small features of a finished artificial tooth to match the tooth arrangement and occlusion of the teeth of a patient. In the course of this operation, an ordinary artificial tooth is difficult to grip, and any tool for this particular purpose remains to be developed. With the projection of the present invention gripped by appropriate perceps, polishing is performed to fine configuration of the artificial tooth 1. Difficult dental laboratory work is thus performed in a labor-saving fashion for a substantially short period of time.

As described above, the artificial tooth has the projection that puts the artificial tooth and the core into temporary bond. The artificial tooth is thus prevented from being misaligned or dislocated from the core in the course of the production of the denture. The proper position of the artificial tooth that is determined in the production of the wax denture is maintained, a highly accurate acrylic resin denture is provided with a yield of the denture substantially improved.

What is claimed is:

1. An artificial tooth comprising:

a selected finished tooth contour; and a projection which is separate and distinct from said finished tooth contour, wherein said projection is temporarily bonded to and removable from a portion of the artificial tooth contour, said projection being of the same type material as the artificial tooth.

2. An artificial tooth according to claim 1, wherein the artificial tooth is made of a synthetic resin.

3. An artificial tooth according to claim 2, wherein the projection is formed by applying, to a finished artificial tooth, a drop of resin that is of the same type as the material of the finished artificial tooth.

4. An artificial tooth according to claim 1, wherein the projection is formed by gluing a resin pellet onto a finished artificial tooth.

5. A method for manufacturing an acrylic resin denture comprising the steps of:

providing a finished artificial tooth;

forming a projection for a temporary bond with a core, on the portion of the finished artificial tooth to be embedded into a core material before the finished artificial tooth is embedded into the core by applying a drop of resin that is of the same type as the material of the artificial tooth, filling a plate resin in the core, and removing the core along with the projection from the finished artificial tooth after the plate resin is polymerized.

6. A method for manufacturing an acrylic resin denture comprising the steps of:

providing a finished artificial tooth;

forming a projection for a temporary bond with a core, on the portion of the finished artificial tooth to be embedded into a core material before the finished artificial tooth is embedded into the core by gluing a resin pellet to the artificial tooth, filling a plate resin in the core; and removing the core along with the projection from the finished artificial tooth after the plate resin is polymerized.

7. A manufacturing method of an acrylic resin denture according to claim 6, wherein the resin pellet is formed by cutting a pellet from a small diameter resin bar.

8. An artificial tooth comprising:

a selected finished tooth contour;

a projection which is separate and distinct from said finished tooth contour, wherein said projection is temporarily bonded to and removable from a portion of the artificial tooth, said projection being of the same type material as the artificial tooth; and a core material, wherein said artificial tooth is embedded into said core material such that the projection holds the tooth in proper position during the course of the manufacture of an acrylic resin denture.

* * * * *